United States Patent
Dreyfus et al.

(10) Patent No.: US 9,068,910 B2
(45) Date of Patent: Jun. 30, 2015

(54) METHOD FOR PREPARING PETROLEUM BASED SAMPLES FOR ANALYSIS OF ELEMENTAL AND ISOTOPIC SPECIES

(75) Inventors: Sebastien L. Dreyfus, Houston, TX (US); Lloyd M. Wenger, Jr., Houston, TX (US); Holger K. Justwan, Houston, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 13/984,912

(22) PCT Filed: Nov. 2, 2011

(86) PCT No.: PCT/US2011/058979
§ 371 (c)(1),
(2), (4) Date: Aug. 12, 2013

(87) PCT Pub. No.: WO2012/141740
PCT Pub. Date: Oct. 18, 2012

(65) Prior Publication Data
US 2014/0020456 A1    Jan. 23, 2014

Related U.S. Application Data

(60) Provisional application No. 61/475,260, filed on Apr. 14, 2011.

(51) Int. Cl.
*G01N 1/38* (2006.01)
*G01N 33/24* (2006.01)
(Continued)

(52) U.S. Cl.
CPC ............... *G01N 1/38* (2013.01); *B01D 17/047* (2013.01); *G01N 33/18* (2013.01); *G01N 33/1826* (2013.01); *G01N 33/24* (2013.01)

(58) Field of Classification Search
CPC ....... B01D 17/047; G01N 1/38; G01N 33/18; G01N 33/1826; G01N 33/24
USPC ......... 436/25, 27, 29, 60, 73, 77, 83, 84, 139, 436/174, 175, 177; 422/68.1, 72, 533; 73/61.59, 863.21
See application file for complete search history.

(56) References Cited

U.S. PATENT DOCUMENTS

| | | |
|---|---|---|
| 2,246,856 A | 6/1941 | Monson et al. |
| 2,543,871 A | 3/1951 | Salathiel |

(Continued)

FOREIGN PATENT DOCUMENTS

| | | |
|---|---|---|
| WO | WO 2008/100614 | 8/2008 |
| WO | WO 2009/048701 | 4/2009 |

*Primary Examiner* — Maureen Wallenhorst
(74) *Attorney, Agent, or Firm* — ExxonMobil Upstream Research Company Law Dept.

(57) ABSTRACT

A method of separating petroleum samples containing a hydrocarbon-soluble elemental species of interest to facilitate analysis of an elemental and/or isotopic signature. A petroleum sample is mixed with a demulsifier and separated, for example by centrifuging, into one or more intermediate organic fractions. The intermediate organic fraction(s) are mixed with a solvent such as water and a second demulsifier, then separated into one or more prepared organic fractions and one or more solvent-based fractions. Some or all of the resulting fractions are then stored for possible further processing. Optionally, the petroleum sample may be spiked with one or more of an organic standard and an inorganic standard, and the solvent may likewise be spiked with an inorganic internal standard, to facilitate later analysis.

13 Claims, 2 Drawing Sheets

(51) Int. Cl.
*B01D 17/04* (2006.01)
*G01N 33/18* (2006.01)

(56) References Cited

U.S. PATENT DOCUMENTS

| | | | |
|---|---|---|---|
| 2,778,777 A * | 1/1957 | Powell | 208/90 |
| 3,052,627 A * | 9/1962 | Lerner | 208/251 R |
| 3,383,325 A | 5/1968 | Seale et al. | |
| 3,847,549 A | 11/1974 | Schorno | |
| 4,439,345 A * | 3/1984 | Duke | 516/141 |
| 4,480,039 A | 10/1984 | Closmann et al. | |
| 4,645,589 A * | 2/1987 | Krambeck et al. | 208/251 R |
| 5,368,819 A | 11/1994 | Dougherty et al. | |
| 5,798,982 A | 8/1998 | He et al. | |
| 6,140,643 A | 10/2000 | Brown et al. | |
| 6,246,963 B1 | 6/2001 | Cross et al. | |
| 6,514,915 B1 | 2/2003 | Beyer et al. | |
| 6,754,588 B2 | 6/2004 | Cross et al. | |
| 6,810,332 B2 | 10/2004 | Harrison | |
| 6,826,483 B1 | 11/2004 | Anderson et al. | |
| 6,985,841 B2 | 1/2006 | Barroux | |
| 7,124,030 B2 | 10/2006 | Ellis | |
| 7,174,254 B2 | 2/2007 | Ellis | |
| 7,210,342 B1 | 5/2007 | Sterner et al. | |
| 7,249,009 B2 | 7/2007 | Ferworn et al. | |
| 7,297,661 B2 | 11/2007 | Beyer et al. | |
| 7,337,660 B2 | 3/2008 | Ibrahim et al. | |
| 7,387,021 B2 | 6/2008 | DiFooggio | |
| 7,395,691 B2 | 7/2008 | Sterner et al. | |
| 7,520,158 B2 | 4/2009 | DiFoggio | |
| 7,526,418 B2 | 4/2009 | Pita et al. | |
| 7,529,626 B1 | 5/2009 | Ellis | |
| 7,640,109 B2 | 12/2009 | Eide et al. | |
| 2005/0256647 A1 | 11/2005 | Ellis | |
| 2006/0014647 A1 | 1/2006 | Beyer et al. | |
| 2006/0052251 A1 | 3/2006 | Anderson et al. | |
| 2006/0235667 A1 | 10/2006 | Fung et al. | |
| 2006/0282243 A1 | 12/2006 | Childs et al. | |
| 2007/0037288 A1 * | 2/2007 | Qian et al. | 436/143 |
| 2007/0048874 A1 | 3/2007 | Schabron et al. | |
| 2008/0040086 A1 | 2/2008 | Betancourt et al. | |
| 2008/0059140 A1 | 3/2008 | Salmon et al. | |
| 2008/0097735 A1 | 4/2008 | Ibrahim et al. | |
| 2008/0099241 A1 | 5/2008 | Ibrahim et al. | |
| 2008/0147326 A1 | 6/2008 | Ellis | |
| 2008/0173804 A1 | 7/2008 | Indo et al. | |
| 2009/0071239 A1 | 3/2009 | Rojas et al. | |

* cited by examiner

US 9,068,910 B2

METHOD FOR PREPARING PETROLEUM BASED SAMPLES FOR ANALYSIS OF ELEMENTAL AND ISOTOPIC SPECIES

CROSS-REFERENCE TO RELATED APPLICATION

This application is the National Stage entry under 35 U.S.C. 371 of PCT/US2011/058979 that published as Intl. Patent App. Pub. No. 2012/141740 and was filed on 2 Nov. 2011, which claims the priority benefit of U.S. Provisional Patent Application 61/475,260 filed 14 Apr. 2011 entitled METHOD FOR PREPARING PETROLEUM BASED SAMPLES FOR ANALYSIS OF ELEMENTAL AND ISOTOPIC SPECIES, the entirety of which is incorporated by reference herein.

FIELD OF THE INVENTION

Embodiments of the present disclosure relate to the field of petroleum geochemistry. More particularly, embodiments relate to methods for preparing a petroleum sample for elemental and/or isotopic signature analysis.

BACKGROUND

This section is intended to introduce various aspects of the art, which may be associated with the present disclosure. This discussion is believed to assist in providing a framework to facilitate a better understanding of particular aspects of the present invention. Accordingly, it should be understood that this section should be read in this light, and not necessarily as admissions of prior art.

Natural petroleum typically includes elements such as, for example, nickel (Ni), vanadium (V), molybdenum (Mo), iron (Fe), cobalt (Co), rhenium (Re), gallium (Ga), osmium (Os), uranium (U), thorium (Th), lead (Pb), or a combination thereof. Various ones of these elements may be so-called major elements, in that they are present in significant concentrations in a given sample, or they may be so-called trace elements.

Elements found in petroleum are typically present in a variety of isotopes. As a well-known example, naturally-occurring uranium often includes at least two isotopes: U-238, which has 92 protons and 146 neutrons; and, in much lower concentrations, U-235, which again has 92 protons but only 143 neutrons.

For various reasons, some of which are described below, major and trace elements occurring in natural petroleum are of interest in the Upstream sector of the petroleum industry (which refers generally to activities relating to the extraction of natural petroleum from deposits). In addition, in the Downstream sector (which refers generally to activities relating to the refining of natural petroleum into specific products such as gasoline, plastics, and the like), certain elements may be analyzed and monitored because of their potential detrimental effects (e.g., potential for disrupting catalytic processes).

Analysis of the elemental and/or isotopic "signatures" of major and trace elements may also be beneficial. Generally speaking, a "signature" of a given sample of material consists of the relative concentrations and/or ratios of various specified elements and/or elemental isotopes. Such signatures can provide important information about the sample. Various kinds of signature analysis are used, for example, in the identification of source environment-of-deposition (EOD) and in oil-oil and oil-source-rock correlation.

Much prior research in this area (for example in oil-source correlation or maturity studies) has tended to focus on the metallic elements nickel (Ni) and vanadium (V). This appears to be due to two factors.

First, Ni and V are commonly abundant in petroleum hydrocarbons. That is to say, Ni and V are commonly abundant in the organic fractions of petroleum, which refers to groups of organic compounds that are associated with natural petroleum such asphatenes, NSO (nitrogen-sulfur-oxygen) fractions, etc. As one illustration of the meaning of the term "associated with" as used in this disclosure, an element, for example Ni or V, is associated with an organic fraction if (i) the element is part of an organic molecule such as a porphyrin (e.g., a nickel porphyrin); or (ii) the element is not part of, but is present with and perhaps bound to, an organic compound.

Second, Ni and V tend to be primarily associated with organic fractions of petroleum and not with inorganic fractions. This largely-binary distribution of Ni and V helps to reduce the potential confusion and ambiguity of analytical results. That is, data obtained from analysis of the elemental signatures of Ni and V are very likely to be associated with organic fractions and not with inorganic fractions in the petroleum sample.

As is well-known to those of ordinary skill in the art, some inorganic fractions associated with petroleum products are aqueous (i.e., water-based), while others are mineral-based. Furthermore, inorganic fractions can be natural in origin, anthropogenic (i.e., human-originated), or a combination of the two.

While Ni and V are among the most-commonly studied elements in this area, they are not the only elements in petroleum that are of potential analytical interest. Certain other elements found in petroleum may also be associated with organic fractions. Some of these other elements include, for example, molybdenum (Mo), iron (Fe), cobalt (Co), rhenium (Re), gallium (Ga), osmium (Os), uranium (U), thorium (Th), and lead (Pb).

When these "other elements" are associated with asphaltene fractions in petroleum, they are typically related directly to the source rock from which the petroleum was generated (i.e., in which the petroleum was created). Such elements therefore could be useful for oil-oil and oil-to-source-rock correlation studies, petroleum dating, and petroleum fluid alteration studies.

However, unlike Ni and V which tend to be associated primarily with organic fractions of petroleum, these "other elements" can be associated not only with organic fractions but also inorganic fractions. Such inorganic association may also be useful. For example, information about water in the petroleum formation and/or anthropogenic inorganic contaminants may be obtained via analysis of these "other elements" in associated aqueous fractions. This lack of a binary distribution, however, can make it difficult to assess which elemental and/or isotopic signatures arise from organic fractions and which from inorganic fractions. Such difficulty, in turn, can complicate or even effectively preclude the use of these "other elements" in the kinds of applications just mentioned. Accordingly, it would be desirable to have a method for separating petroleum samples containing hydrocarbon-soluble elemental species of interest, to facilitate differentiation between organic and inorganic elemental species in signature analysis of natural tracers (i.e., deconvoluted analysis of elemental and/or isotropic signature).

SUMMARY

A method of preparing a petroleum sample for use with one or more of elemental and isotopic signature analysis is provided in the present disclosure. The method comprises the steps of (a) adding a first demulsifier to the petroleum sample, said first demulsifier having a known concentration of a specified hydrocarbon-soluble elemental species referred to as a species of interest; (b) separating the petroleum sample into one or more intermediate organic fractions; (c) mixing the one or more intermediate organic fractions with at least one of (i) a solvent in which a specified inorganic contaminant species is soluble and having a known concentration of the species of interest, and (ii) a second demulsifier having a known concentration of the species of interest; and (d) separating the one or more intermediate organic fractions into one or more prepared organic fractions and one more solvent-based fractions.

In another embodiment of the present disclosure, a method is provided comprising the steps of (a) adding to a petroleum sample (i) a first demulsifier, said first demulsifier being substantially free of a specified hydrocarbon-soluble elemental species referred to as a species of interest, and (ii) one or more of an inorganic standard and an organic standard, each said standard having a known concentration of a respective marker of which the sample is substantially free; (b) separating the sample into one or more intermediate organic fractions; (c) mixing the one or more intermediate organic fractions with (i) highly-pure deionized water; (ii) a second demulsifier substantially free of the species of interest; and (iii) an inorganic internal standard having a known concentration of a marker of which the sample is substantially free; and (d) separating the one or more intermediate organic fractions into one or more prepared organic fractions and one or more water-based fractions.

In yet another embodiment of the present disclosure, a method is provided for preparing a petroleum sample, said petroleum sample potentially containing (i) a specified hydrocarbon-soluble elemental species referred to as a species of interest, and (ii) an inorganic contaminant species that includes the species of interest. The method comprises the steps of (a) dissolving the petroleum sample in a solvent in which the specified hydrocarbon-soluble elemental species are soluble but the inorganic contaminant species are not soluble; and (b) separating the petroleum sample into one or more organic fraction.

BRIEF DESCRIPTION OF THE DRAWINGS

The foregoing and other advantages of the present disclosure may become apparent upon reviewing the following detailed description and drawings of non-limiting examples of embodiments in which.

DETAILED DESCRIPTION DEFINITIONS

Various terms as used herein are defined below. To the extent a term used in a claim is not defined below, it should be given the definition persons in the pertinent art have given that term.

As used herein, the "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprised," and "comprise" are open-ended transition terms used to transition from a subject recited before the term to one or more elements recited after the term, where the element or elements listed after the transition term are not necessarily the only elements that make up of the subject.

As used herein, the terms "containing," "contains," and "contain" have the same open-ended meaning as "comprising," "comprises," and "comprise."

As used herein, the term "exemplary" means "serving as an example, instance, or illustration." Any embodiment described herein as "exemplary" is not necessarily to be construed as preferred or advantageous over other embodiments.

As used herein, the terms "having," "has," and "have" have the same open-ended meaning as "comprising," "comprises," and "comprise."

As used herein, the terms "including," "includes," and "include" have the same open-ended meaning as "comprising," "comprises," and "comprise."

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

DETAILED DESCRIPTION

In the following detailed description section, specific embodiments of the present invention are described in connection with preferred embodiments. However, to the extent that the following description is specific to a particular embodiment or a particular use of the present invention, this is intended to be for example purposes only. Accordingly, the invention is not limited to the specific embodiments described below, but rather, it includes all alternatives, modifications, and equivalents falling within the true spirit and scope of the appended claims.

Figure 1:
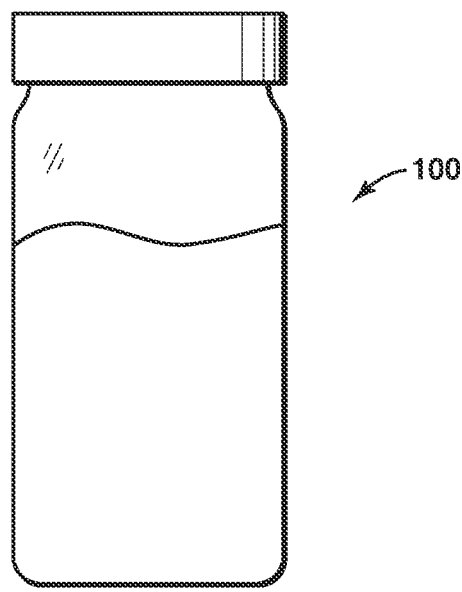
FIG. 1 illustrates a view of a petroleum sample prior to application of the present invention.

With reference to FIG. 1, an initial sample 100 is shown in accordance with at least one embodiment of the present invention. In general, the initial sample 100 is thought to comprise at least one hydrocarbon-soluble elemental species, referred to as a "species of interest", that may be used as a natural tracer. The species of interest might be an organo-elemental compound such as, for example, a vanadium-, nickel-, or iron porphyrin, but it could be any organo-elemental compound. The term "natural tracer" refers here to an element, isotope, compound, or other hydrocarbon-soluble substance that is present naturally in the petroleum sample 100 and is of analytical interest. Examples of natural tracers include but are not limited to concentrations and isotopic signatures of molybdenum, iron, cobalt, rhenium, gallium, osmium, uranium, thorium, and lead. A given petroleum sample could include multiple natural tracers.

The petroleum sample 100 may also include one or more inorganic contaminant species which may, themselves, include the elemental species of interest. Such contaminants may be introduced, for example, by drilling fluids, drilling additives, corrosion, formation water, and the like. It may be noted that if a given sample were known to be devoid of any contaminants containing the natural tracer, then the preparation of the given sample in accordance with the present invention may generally be reduced or eliminated. In practice, however, one can seldom if ever be certain that a given sample is devoid of a particular substance. Accordingly, a practitioner may elect to prepare a sample as described in the present disclosure even if the sample turns out to have been devoid of contaminants.

Figure 2:
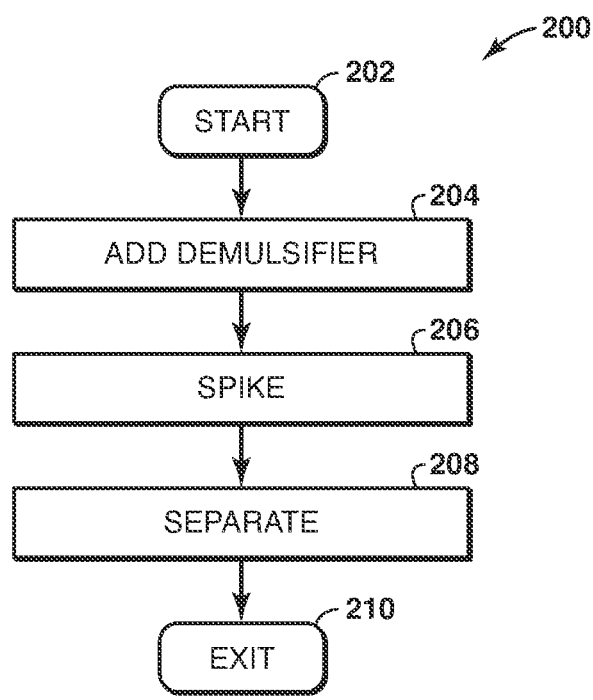
FIG. 2 is a flow diagram of a method in accordance with an embodiment of the present invention.

Referring to FIG. 2, a flow diagram of a method 200 for preparing a sample (e.g., sample 100) in accordance with an embodiment of the present invention is shown. The method 200 generally includes a plurality of blocks or steps (e.g., 202, 204, 206, 208, 210) that may be performed serially. As will be appreciated by one of ordinary skill in the art, the order of the steps shown in FIG. 2 is exemplary and the order of one or more steps may be modified within the spirit and scope of the present invention. Additionally, the steps of the method 200 may be performed in at least one non-serial (or non-sequential) order, and one or more steps may be omitted to meet the design criteria of a particular application.

Step 202 represents an entry point into the method 200.

At step 204, a suitable demulsifier may be added to the sample to help separate a water fraction and/or any other inorganic fraction(s) from the organic fractions of the petroleum sample. Preferably the demulsifier is devoid of the elemental species of interest. However, the demulsifier may include the elemental species of interest if the concentration of the species of interest in the demulsifier is known or may be determined Any appropriate demulsifier may be used to satisfy the design criteria of a particular application. In general the selection of a specific demulsifier will depend on factors such as cost, demulsification efficiency, and the like, as is well known to those of ordinary skill having the benefit of this disclosure.

At step 206 the sample may be "spiked" by adding one or more organic standard, inorganic standard, or both. In this context, the term "spiked" refers to the process of mixing a known substance into the sample. Furthermore, in this context a "standard" may be a substance (e.g., solid or liquid) having a known (and, generally, a certified) composition comprising one or more markers (i.e., one or more elements, isotopes, compounds, or the like not naturally present in the sample) for later use as an internal tracer or reference point. Standards of this kind are commercially available and are well-known in the art. In one embodiment, an organic standard may be, for example, a certified trace-element concentration of uranium, thorium, or bismuth, in an organic solvent such as xylene. Similarly, an inorganic standard might be, for example, a similar trace-element concentration in an aqueous (water-based) solution. As will be understood by those of ordinary skill in the art having the benefit of this disclosure, measurement of various marker concentrations in organic and/or inorganic fractions can assist in tracking the efficiency of the sample separation process and/or to determine more precisely the amounts of the fractions recovered after sample preparation. Depending on, for example, the design requirements of a specific embodiment, relevant chemical limitations, relevant physical limitations, and/or the like; one or more standards (i) may be mixed into the sample either before and/or after the demulsifier is mixed in (i.e., prior to and/or following step 204), or (ii) might be mixed into the demulsifier instead of directly into the sample.

At step 208 the sample may be separated. In at least one embodiment the sample may be separated by centrifuging the sample. In at least one other embodiment, the sample may be separated into one or more components via density separation (i.e., letting the sample sit for a period of time to allow the fractions to separate via gravity, much as an oil-and-vinegar salad dressing will separate over time.) However, any appropriate separation technique may be used to satisfy the design criteria of a particular application.

Step 210 represents an exit point out of the method 200.

Figure 3:
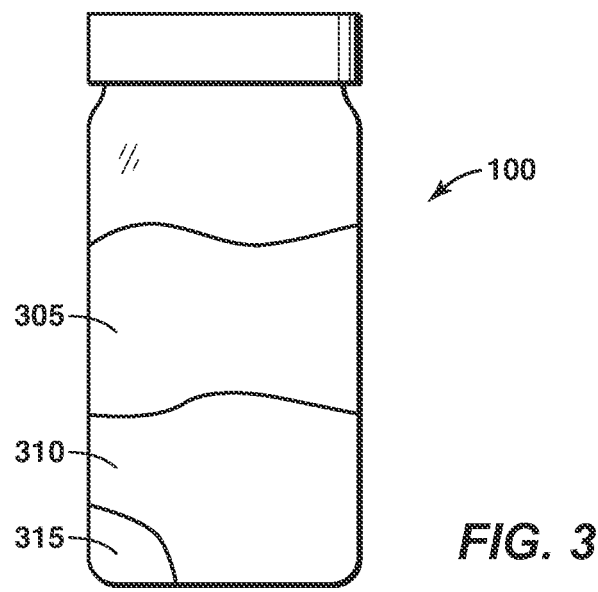
FIG. 3 illustrates a view of a petroleum sample in accordance with an embodiment of the present invention after application of the method of FIG. 2.

Referring now to FIG. 3, the initial sample 100 is shown in a separated state (e.g., following step 208 of method 200) in accordance with at least one embodiment of the present invention. In at least one embodiment, the sample 100 is separated into one or more organic fractions, referred to as one or more intermediate organic fractions 305, and (if present) one or more inorganic fractions 310 such as a water-based fraction. A solid (e.g., mineral) fraction 315 may also result from the separation technique. The intermediate organic fractions 305 will generally include one or more organic compounds with which the species of interest is associated. The inorganic fraction(s) 310, if any, will typically be water-based, and may also be associated with the species of interest.

Figure 4:
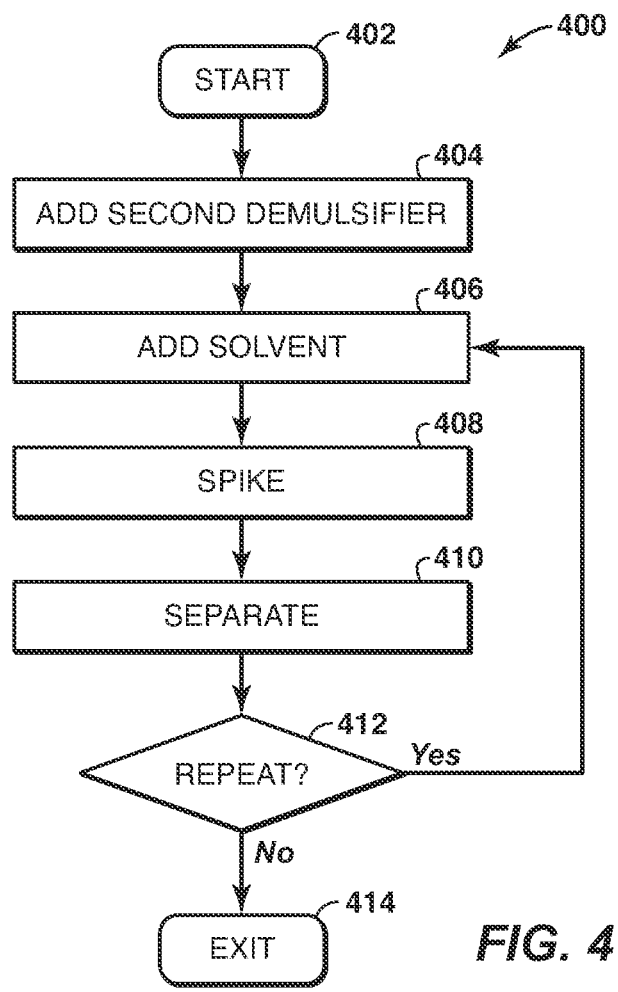
FIG. 4 is a flow diagram of a method in accordance with an embodiment of the present invention.

Referring to FIG. 4, a flow diagram of a method 400 for preparing or further preparing a sample (e.g., sample 100) in accordance with an embodiment of the present invention is shown. The method 400 may be advantageously implemented in connection with the method 200, described previously in connection with FIG. 2, and/or any appropriate system and/or method to meet the design criteria of a particular application. The method 200 generally includes a plurality of blocks or steps (e.g., 402, 404, 406, 408, 410, 412, 414) that may be performed serially. As will be appreciated by one of ordinary skill in the art, the order of the steps shown in FIG. 4 is exemplary and the order of one or more steps may be modified within the spirit and scope of the present invention. Additionally, the steps of the method 400 may be performed in at least one non-serial (or non-sequential) order, and one or more steps may be omitted to meet the design criteria of a particular application.

Step 402 represents an entry point into the method 400.

At step 404 a second demulsifier may be mixed into one or more intermediate organic fraction (e.g., 305). Preferably the second demulsifier is devoid of the elemental species of interest. However, the second demulsifier may include the elemental species of interest if the concentration of the species of interest in the second demulsifier is known or may be determined. In at least one embodiment the second demulsifier may be the same demulsifier added during step 204 of method 200. However, any appropriate demulsifier may be used to satisfy the design criteria of a particular application.

At step 406 a solvent may be mixed into the intermediate organic fraction. In at least one embodiment the solvent is a water-based solvent that does not include the species of interest and in which the intermediate organic fraction(s) are not soluble. In general, the solvent is used to "wash" those fractions to remove any inorganic contaminant species present in the fractions that are soluble in the solvent. One suitable solvent, for example, may be highly-pure deionized water. However, any appropriate solvent may be used to satisfy the design criteria of a particular application.

At step 408 the intermediate organic fraction may be spiked by adding a standard, preferably an inorganic internal standard. For example, a solution of one-hundred-parts-perbillion of yttrium in water may be added to aid in assessing the efficiency of the separation process and in quantifying water-fraction and organic-fraction amounts. In at least one embodiment the standard may be mixed into the solvent before the solvent is mixed into the intermediate organic fractions (i.e., prior to step 406). Depending on, for example, the design requirements of a specific embodiment, however; one or more suitable standards (i) may be mixed (i) directly into the intermediate organic fractions before or after the solvent is added, (ii) into the second demulsifier of step 404, and/or (iii) into the solvent of step 406.

At step 410 the intermediate organic fractions mixture, which includes in the mixture at least the second demulsifier and the solvent, is separated into fractions using any appropriate technique such as centrifuging or density separation. The result of the separation process is one or more prepared organic fractions and a solvent-based fraction. In effect, the mixing (e.g., steps 404, 406 and/or 408) and separation (e.g., step 410) has the effect of washing the intermediate organic fractions (e.g., 305) with solvent to remove a sufficient portion of any inorganic species that have been present; thereby producing the prepared organic fractions and the solvent-based fraction.

It may be appreciated that multiple inorganic contaminant species may be present in a given intermediate organic fraction. Accordingly, the solvent applied at step 406 might not dissolve all of the contaminant species. In such a case, the intermediate organic fraction(s) may be "washed" with multiple solvents in the general manner just described. The multiple washings may be carried out in series, that is, one after another, with each successive washing producing one or more new prepared organic fractions and one or more new solvent-based fractions. Alternatively or in addition, depending on the application and the analytical needs, multiple solvents may be used simultaneously, possibly resulting in multiple solvent-based fractions being produced during separation. This iterative process is represented by decision block 412.

The efficiency of the separation process may be monitored by comparing (i) the elemental and/or isotopic signatures of the marker(s) in the various fractions produced above, with (ii) the corresponding signatures in the organic and inorganic standards. Such monitoring may allow for quantification of the volume of organic and inorganic fractions present in, or associated with, the unprepared, initial sample.

The following describes an example of a specific procedure for preparing a petroleum sample in accordance with the methods of the foregoing. It should be appreciated that this example is not intended to limit the scope of the invention as that invention is specified in the appended claims. It may also be appreciated by those of ordinary skill in the art having the benefit of this disclosure that all parameters such as amounts, times, etc., may be varied to meet the design criteria of a particular application. This example assumes an initial petroleum sample comprising heavy oil or organic solids (e.g. asphaltenes, bitumen).

Dissolve 500 mg of the initial petroleum sample in 10 ml of organic solvent (e.g. xylene, toluene, dichloromethane) and mix thoroughly. For clarity, the term "sample" in the remaining paragraphs of this example refers to this solution of organic solvent and the initial petroleum sample.

Pour the sample into a centrifuge tube that has been pre-cleaned with xylene.

Spike the sample with 100 parts per billion (ppb=$ng \cdot g^{-1}$) of organic bismuth internal [standard] and 100 parts per billion (ppb=$ng \cdot g^{-1}$) of inorganic terbium internal standard.

Add 2 drops of demulsifier to the sample and mix thoroughly.

Centrifuge the sample for 30 minutes at 40° C. and 10,000 rpm.

Carefully transfer the hydrocarbon-based fraction (i.e., intermediate organic fraction) into another centrifuge tube pre-cleaned with xylene. Store any water-based and/or sold fractions in glass or Teflon jars pre-cleaned with both xylene and nitric acid.

For every one part of the organic fraction (by volume), add two parts of ultra-pure water for a 1:2 ratio. The ultra-pure water may optionally be spiked with 100 parts per billion (ppb=$ng \cdot g^{-1}$) of inorganic yttrium internal standard to help in quantifying any ultra-pure water that might become associated with one or more organic fractions during this process.

Add 2 drops of metal-free demulsifier to the sample and mix thoroughly.

Centrifuge again for 30 minutes at 40° C. and 10,000 rpm.

Carefully transfer the hydrocarbon-based fraction (which will be the supernatant fraction, floating above the water-based fraction) and the water-based fraction into separate glass or Teflon jars that have been pre-cleaned with xylene and nitric acid.

Evaporate the organic-solvent content using a slow stream of ultra-high-purity (UHP) nitrogen. It may be appreciated that this step may not be necessary; especially in cases where the initial sample was not diluted because, for example, the initial sample did not include heavy oil or organic solids.

Analyze, to the extent necessary or desired to satisfy the design criteria of a particular application, each of the fractions for their respective elemental and/or isotopic signatures.

In one or more embodiments of the present invention it may be preferable to forego one or more of the above described steps and simply mix a petroleum sample with a suitable quantity of a solvent in which organic fractions are soluble (for example, xylene). In such an embodiment, the sample's dissolved organic fractions may be made significantly lighter than the sample's inorganic fractions. The resulting mixture may then be separated, e.g., by centrifuging, and the solvent may be evaporated from the organic fractions as described above.

Those of ordinary skill in the art having the benefit of this disclosure will recognize that analysis of elemental and/or isotopic signatures in the various fractions of a sample (e.g., 100) may be used in a number of different applications. A few are mentioned below for purposes of illustration; it is assumed that those of ordinary skill are or can readily become familiar with the details in light of the above present disclosure.

As a first example, the invention may be beneficial in the identification of source-rock environment of deposition (EOD). Hydrocarbon-soluble trace elements such as nickel, vanadium, molybdenum, iron, cobalt, gallium, and uranium are generally directly related to the source rock. The incorporation of such trace elements in the organic matter of the source rock is highly sensitive to the Eh-pH conditions and clay content of the environment of deposition. The distribution of these hydrocarbon-soluble species in the petroleum may, therefore, be useful in reconstructing the depositional environment of their source. Without the present invention to properly isolate these specific hydrocarbon-soluble elements, however, reliance on assessments of bulk concentrations of these elements would likely lead to inaccurate interpretations.

Another potential application for the present invention is the field of dating expulsion/generation of petroleum. Geochronometers are promising tools for dating petroleum expulsion/generation. Hydrocarbon-soluble trace elements like Re, Os, U, Th, and Pb are generally directly related to the source rock and could, therefore, be used as radiometric chronometers for petroleum generation/expulsion dating. However, these trace element species can be easily contaminated by inorganic species associated with inorganic fluids and solids. Such contamination may result in the determination of erroneous ages. Accordingly, the present invention may be used to increase the accuracy of such test results.

The present invention may be susceptible to various modifications and alternative forms and the exemplary embodiments discussed above have been shown only by way of example. It should be understood that the invention is not intended to be limited to the particular embodiments disclosed herein. Indeed, the present invention includes all alternatives, modifications, and equivalents falling within the true spirit and scope of the appended claims.

What is claimed is:

1. A method of preparing a petroleum sample having an inorganic contaminant species for use with one or more of elemental and isotopic signature analysis, comprising:
    (a) adding a first demulsifier to the petroleum sample, said first demulsifier having a known concentration of a specified hydrocarbon-soluble elemental species referred to as a species of interest;
    (b) separating the petroleum sample into one or more intermediate organic fractions and one or more inorganic fractions;
    (c) mixing the one or more intermediate organic fractions with (i) a solvent in which the inorganic contaminant species is soluble and the solvent has a known concentration of the species of interest, and (ii) a second demulsifier having a known concentration of the species of interest;
    (d) separating the one or more intermediate organic fractions into one or more prepared organic fractions and one or more solvent-based fractions; and
    (e) determining at least one of an elemental signature and an isotopic signature from the one or more prepared organic fractions.

2. The method of claim 1, wherein one or more of the known concentrations of the species of interest in the first demulsifier, the second demulsifier, and the solvent are substantially zero.

3. The method of claim 1, further comprising, before separating the petroleum sample, spiking the petroleum sample with one or more of an inorganic standard and an organic standard, each said standard having a known concentration of a respective marker of which the petroleum sample is substantially free.

4. The method of claim 1, wherein the solvent is pure deionized water.

5. The method of claim 1 wherein the first demulsifier and the second demulsifier are substantially the same substance.

6. The method of claim 1, further comprising, before separating the intermediate organic fractions, spiking the intermediate organic fractions with an inorganic internal standard having a known concentration of a specified marker of which the petroleum sample is substantially free.

7. The method of claim 6, wherein the intermediate organic fractions are spiked with an inorganic internal standard by spiking the solvent with the inorganic internal standard.

8. The method of claim 1, further comprising additionally processing the prepared organic fractions by re-performing the operations described in steps (c) and (d) with the prepared organic fractions in the place of the intermediate organic fractions.

9. A method of preparing a petroleum sample having an organic and an inorganic fraction for use with one or more of elemental and isotopic signature analysis, comprising:
    (a) adding to the sample: (i) a first demulsifier, said first demulsifier being substantially free of a specified hydrocarbon-soluble elemental species referred to as a species of interest, and (ii) one or more of an inorganic standard and an organic standard, each said standard having a known concentration of a respective marker of which the sample is substantially free;
    (b) separating the sample into one or more intermediate organic fractions and one or more inorganic fractions;
    (c) mixing the one or more intermediate organic fractions with (i) highly-pure deionized water; (ii) a second demulsifier substantially free of the species of interest; and (iii) an inorganic internal standard having a known concentration of a marker of which the sample is substantially free;
    (d) separating the one or more intermediate organic fractions into one or more prepared organic fractions and one or more water-based fractions; and
    (e) determining at least one of an elemental signature and an isotopic signature from the one or more prepared organic fractions.

10. A method of preparing a petroleum sample, said petroleum sample containing (i) an organic fraction containing a specified hydrocarbon-soluble elemental species referred to as a species of interest, and (ii) an inorganic contaminant fraction that includes the species of interest; said method comprising:
    (a) dissolving the petroleum sample in a solvent in which the organic fraction is soluble but the inorganic contaminant fraction is not soluble;
    (b) separating the petroleum sample into one or more organic fractions; and
    (c) separating the petroleum sample into one or more inorganic fractions.

11. The method of claim 10, further comprising, before separating the petroleum sample, spiking the petroleum sample with one or more of an inorganic standard and an organic standard, each of the one or more standards having a known concentration of a respective marker of which the petroleum sample is substantially free.

12. The method of claim 10 further comprising the step of determining an elemental signature from the one or more organic fractions.

13. The method of claim 10 further comprising the step of determining an isotopic signature from the one or more organic fractions.

* * * * *